United States Patent
Rüfer et al.

(10) Patent No.: US 9,868,702 B2
(45) Date of Patent: Jan. 16, 2018

(54) PROCESS FOR PRODUCING 2-(2,2,6,6-TETRAMETHYLPIPERIDIN-4-YL)PROPANE-1,3-DIAMINE

(71) Applicant: Evonik Degussa GmbH, Essen (DE)

(72) Inventors: Alexander Martin Rüfer, Recklinghausen (DE); Anne Rittsteiger, Olfen (DE); Jörg-Joachim Nitz, Essen (DE); Stephan Kohlstruk, Gladbeck (DE); Martina Ortelt, Flein (DE); Dirk Fuchsmann, Haltern am See (DE); Michael Demming, Dülmen (DE); Christine Stemmer, Marl (DE); Denise Ott, Marl (DE); Anja Stasch, Recklinghausen (DE)

(73) Assignee: Evonik Degussa GmbH, Essen (DE)

(*) Notice: Subject to any disclaimer, the term of this patent is extended or adjusted under 35 U.S.C. 154(b) by 0 days.

(21) Appl. No.: 15/605,268

(22) Filed: May 25, 2017

(65) Prior Publication Data
US 2017/0355674 A1    Dec. 14, 2017

(30) Foreign Application Priority Data
Jun. 10, 2016 (EP) .................... 16173860

(51) Int. Cl.
*C07D 211/26* (2006.01)
*C08G 59/50* (2006.01)

(52) U.S. Cl.
CPC .......... *C07D 211/26* (2013.01); *C08G 59/506* (2013.01)

(58) Field of Classification Search
None
See application file for complete search history.

(56) References Cited

U.S. PATENT DOCUMENTS

| | | |
|---|---|---|
| 3,030,247 A | 4/1962 | Schurb |
| 3,386,955 A | 6/1968 | Chrobok et al. |
| 3,536,720 A | 10/1970 | Murayama et al. |
| 3,677,978 A | 7/1972 | Dowbenko |
| 3,678,007 A | 7/1972 | Dowbenko |
| 4,283,520 A | 8/1981 | Moser et al. |
| 4,436,892 A | 3/1984 | Zondler et al. |
| 4,529,821 A | 7/1985 | Stockinger et al. |
| 4,550,203 A | 10/1985 | Stockinger et al. |
| 4,587,311 A | 5/1986 | Schmid et al. |
| 4,618,712 A | 10/1986 | Stockinger et al. |
| 4,694,096 A | 9/1987 | Lehmann et al. |
| 4,859,761 A | 8/1989 | Flury et al. |
| 5,352,831 A | 10/1994 | Flury et al. |
| 5,424,373 A | 6/1995 | Flury et al. |
| 5,523,362 A | 6/1996 | Flury et al. |
| 6,613,861 B2 | 9/2003 | Gras |
| 6,908,980 B2 | 6/2005 | Gras |
| 6,916,897 B2 | 7/2005 | Gras |
| 6,924,385 B2 | 8/2005 | Lettmann et al. |
| 9,085,506 B2 | 7/2015 | Galle et al. |
| 2008/0045738 A1 | 2/2008 | Orschel et al. |
| 2013/0041103 A1 | 2/2013 | Grenda et al. |
| 2015/0353491 A1 | 12/2015 | Jaegli et al. |
| 2016/0289164 A1 | 10/2016 | Kohlstruk et al. |

FOREIGN PATENT DOCUMENTS

| | | |
|---|---|---|
| CA | 2145589 A1 | 9/1995 |
| DE | 1695749 A1 | 4/1971 |
| EP | 306451 A2 | 3/1989 |
| EP | 669353 A1 | 8/1995 |
| EP | 675185 A2 | 10/1995 |
| WO | 9955772 A1 | 11/1999 |
| WO | 2005087705 A1 | 9/2005 |
| WO | 2014118121 A1 | 8/2014 |
| WO | 2016120235 A1 | 8/2016 |

OTHER PUBLICATIONS

European Search Report dated Aug. 23, 2016 in EP 16 17 3860 (1 page).
Langkabel et al., U.S. Appl. No. 15/602,723, filed May 23, 2017.
Langkabel et al., U.S. Appl. No. 15/604,118, filed May 24, 2017.
Rittsteiger et al., U.S. Appl. No. 15/473,892, filed Mar. 30, 2017.
Rüfer et al., U.S. Appl. No. 15/603,966, filed May 24, 2017.
Rüfer et al., U.S. Appl. No. 15/604,873, filed May 25, 2017.
Rüfer et al., U.S. Appl. No. 15/604,988, filed May 25, 2017.

*Primary Examiner* — Sudhakar Katakam
*Assistant Examiner* — Ana Z Muresan
(74) *Attorney, Agent, or Firm* — Philip P. McCann; Smith Moore Leatherwood LLP

(57) ABSTRACT

A process for producing 2-(2,2,6,6-tetramethylpiperidin-4-yl)propane-1,3-diamine by A) reacting triacetonamine (TAA) and malononitrile to afford the intermediate 2-(2,2,6,6-tetramethylpiperidin-4-ylidene)malononitrile, and B) hydrogenating 2-(2,2,6,6-tetramethylpiperidin-4-ylidene) malononitrile in the presence of at least one catalyst. In another embodiment, the hydrogenation in step B) of the process is performed at 20-120° C. and at 20-300 bar. In another embodiment, the hydrogenation in step B) of the process is performed in two stages at 20-120° C. and at 20-300 bar.

19 Claims, No Drawings

PROCESS FOR PRODUCING 2-(2,2,6,6-TETRAMETHYLPIPERIDIN-4-YL)PROPANE-1,3-DIAMINE

This application claims the benefit of European Application No. 16173860.4 filed on Jun. 10, 2016, the disclosure of which is expressly incorporated herein by reference.

BACKGROUND

The present invention relates to a process for producing 2-(2,2,6,6-tetramethylpiperidin-4-yl)propane-1,3-diamine, which can be used as hardener in epoxide applications.

2-(2,2,6,6-tetramethylpiperidin-4-yl)propane-1,3-diamine (TMP-PDA) has the chemical structure depicted in formula 1.

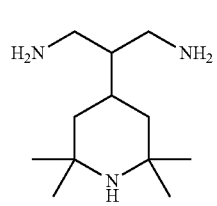

formula 1

2-(2,2,6,6-tetramethylpiperidin-4-yl)propane-1,3-diamine (TMP-PDA)

It is known that amines may be employed as hardeners in epoxy systems. Epoxy resins are prepolymers comprising two or more epoxy groups per molecule. The reaction of these resins with a range of hardeners affords crosslinked polymers. An overview of possible resins and hardeners, their use and properties is given in H. Schumann, "*Handbuch Betonschutz durch Beschichtung*", Expert Verlag 1992, pages 396-428.

SUMMARY

It is an object of the invention to find a process for producing 2-(2,2,6,6-tetramethylpiperidin-4-yl)propane-1,3-diamine.

It is also an object of the invention to find a novel amine suitable for hardening epoxy systems.

DETAILED DESCRIPTION

The invention provides a process for producing 2-(2,2,6,6-tetramethylpiperidin-4-yl)propane-1,3-diamine by
A) reacting triacetonamine (TAA) and malononitrile to afford the intermediate 2-(2,2,6,6-tetramethylpiperidin-4-ylidene)malononitrile, and
B) hydrogenating 2-(2,2,6,6-tetramethylpiperidin-4-ylidene)malononitrile in the presence of at least one catalyst.

The production of the compound according to the invention 2-(2,2,6,6-tetramethylpiperidin-4-yl)propane-1,3-diamine proceeds in step A) via a Knoevenagel condensation between triacetonamine (TAA) and malononitrile. The reaction may be performed in a solvent or in a solvent-free reaction system under mild reaction conditions, preferably at 20-40° C. and atmospheric pressure. The catalyst employed is preferably zirconyl chloride or piperidine. After complete conversion of the reactants the intermediate 2-(2,2,6,6-tetramethylpiperidin-4-ylidene)malononitrile (cf. structure formula 2 in Example 1) may be precipitated out as solid by cooling the reaction solution. A further purification may be effected by distillation for example.

The production of TMP-PDA from 2-(2,2,6,6-tetramethylpiperidin-4-ylidene)malononitrile is effected in step B) by hydrogenation which may be performed in one or more stages. When a plurality of hydrogenation reactions are used the individual stages may be performed in a reactor having different catalyst zones or in a plurality of separate or serially connected reactors. The hydrogenation is preferably effected in fixed-bed reactors. Suitable reactor types are, for example, shaft furnaces, tray reactors or shell and tube reactors. It is also possible to connect a plurality of fixed-bed reactors in series for the hydrogenation, each of the reactors being operated in downflow mode or in upflow mode as desired.

The catalysts employed may in principle be any catalysts which catalyze the hydrogenation of nitrile groups with hydrogen. Particularly suitable catalysts are nickel, copper, iron, palladium, rhodium, ruthenium and cobalt catalysts, very particularly palladium, ruthenium and cobalt catalysts. To increase activity, selectivity and/or service life, the catalysts may comprise additional doping metals or other modifiers. Typical doping metals are, for example, Mo, Fe, Ag, Cr, Ni, V, Ga, In, Bi, Ti, Zr and Mn, and the rare earths. Typical modifiers are, for example, those with which the acid-base properties of the catalysts can be influenced, preferably alkali metals and alkaline earth metals or compounds thereof, preferably magnesium and calcium compounds, and also phosphoric acid or sulphuric acid and compounds thereof.

The catalysts may be employed in the form of powders or shaped bodies, for example extrudates or compressed powders. It is possible to employ unsupported catalysts, Raney-type catalysts or supported catalysts. Preference is given to Raney-type and supported catalysts. Suitable support materials are, for example, silicon dioxide, aluminium oxide, aluminosilicates, titanium dioxide, zirconium dioxide, kieselguhr, aluminium-silicon mixed oxides, magnesium oxide and activated carbon. The active metal can be applied to the support material in a manner known to those skilled in the art, for example by impregnation, spray application or precipitation. Depending on the method of catalyst production, further preparation steps known to those skilled in the art are necessary, for example drying, calcining, shaping and activation. Further assistants, for example graphite or magnesium stearate, may optionally be added for shaping. The required volume of the hydrogenation catalysts to be used is determined by the LHSV value (liquid hourly space velocity) which is dependent on operating pressure, temperature, concentration and catalyst activity and must be adhered to in order to ensure as complete a hydrogenation as possible.

Production of the inventive diamine TMP-PDA preferably employs hydrogenation catalysts based on palladium and/or cobalt. These catalysts show particularly good activity to achieve a high yield.

The catalysts may be employed in the form of powders or fixed-bed catalysts. The hydrogenation may be effected in batch mode or in continuously operated plants.

The reaction conditions for the hydrogenation are between 20-120° C. and 20-300 bar.

The hydrogenation may be performed in one or more stages. The hydrogenation is preferably performed in two stages. In the first of these stages, reaction conditions of 20-120° C. and 20-300 bar, preferably 40-100° C. and 25-150 bar and particularly preferably 60-90° C. and 40-80 bar are chosen. In the second stage of the hydrogenation, reaction conditions of 20-120° C. and 20-300 bar, preferably 50-115° C. and 50-200 bar and particularly preferably 80-110° C. and 80-140 bar are chosen.

The first stage of the hydrogenation preferably employs a palladium catalyst.

The second stage of the hydrogenation preferably employs a Raney-type catalyst. It is particularly preferable when after activation the catalyst in its entirety has the following composition in weight percent (wt %), the proportions summing to 100 wt % based on the metals present:
cobalt: 57 to 84 wt %
aluminium: 10 to 40 wt %
chromium: 1 to 2 wt %
nickel: 2 to 4 wt %
and
with particle sizes of the catalyst, i.e. of the pellet particles, having a statistical distribution between 3 to 7 millimeters (mm), wherein up to 10 percent of the particles may also be outside the stated range of the stated lower limit or upper limit but also in each case up to 10 percent may be outside the stated range of the stated lower limit and upper limit.

The reaction mixture leaving the hydrogenation is further purified by customary methods to obtain TMP-PDA of the desired quality. Any standard separation methods, for example distillation, flash evaporation, crystallization, extraction, sorption, permeation, phase separation or combinations of the above, may be employed here. The purification may be conducted continuously, batchwise, in one or more stages, under vacuum or under pressure. The purification of TMP-PDA is preferably performed by distillation, for example.

The purification is preferably achieved by distillation under pressure and/or under vacuum in a plurality of steps. Any desired distillation columns with or without internals may be used to this end, for example dephlegmators, dividing walls, unordered internals or random packings, ordered internals or structured packings, or trays with or without forced flow.

Use as epoxy hardener:

The invention also provides for the use of 2-(2,2,6,6-tetramethylpiperidin-4-yl)propane-1,3-diamine (TMP-PDA) as a hardener in epoxy resin compositions.

Contemplated as the epoxy resin component are in principle all epoxy resins that may be cured with amines. Epoxy resins include, for example, polyepoxides based on bisphenol A diglycidyl ether, bisphenol F diglycidyl ether or cycloaliphatic types. However, preference is given to using epoxy resins based on bisphenol A and optionally those based on bisphenol F, optionally also in admixture. The resins and hardeners are preferably employed in equivalent amounts. However, deviations from the stoichiometric ratio are also possible.

EXAMPLES

Example 1: Production of 2-(2,2,6,6-tetramethylpiperidin-4-yl)propane-1,3-diamine, TMP-PDA Step A): Synthesis of 2-(2,2,6,6-tetramethylpiperidin-4-ylidene)malononitrile Formula 2

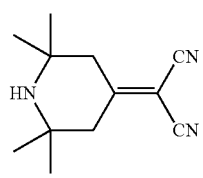

2-(2,2,6,6-tetramethylpiperidin-4-ylidene)malononitrile

A 1 L three-necked flask fitted with two dropping funnels was initially charged with 384.5 g of triacetonamine (TAA) in 350 g of dioxane. The reactor contents were kept at room temperature.

148.5 g of malononitrile were diluted with 150 g of dioxane and initially charged into a dropping funnel.

1.5 g of zirconyl chloride (catalyst) were dissolved in 30 g of deionized water and filled into the second dropping funnel.

The contents of both dropping funnels were then simultaneously added dropwise to the reactor and the reactor was then stirred for one hour at room temperature (between 20-30° C.).

The reaction mixture formed was cooled with an ice bath and the thus precipitated product 2-(2,2,6,6-tetramethylpiperidin-4-ylidene)malononitrile was filtered off.

The further purification was effected by recrystallization in a solvent mixture of 50 wt % of cold ethanol and 50 wt % of cold deionized water and subsequent filtration and drying in a vacuum drying cabinet (45° C., 10 mbar, 3 h).

The product composition was determined by gas chromatography.

The yield of 2-(2,2,6,6-tetramethylpiperidin-4-ylidene)malononitrile was 90%.

Step B1): Partial Hydrogenation of 2-(2,2,6,6-tetramethylpiperidin-4-ylidene)malononitrile to Produce TMP-PDA, 1st Hydrogenation Stage 150 ml of the fixed-bed catalyst Pd/aluminium oxide (1 wt % Pd) was installed in a 2 L pressure autoclave fitted with a catalyst cage.

1 L of solution comprising 10 wt % of 2-(2,2,6,6-tetramethylpiperidin-4-ylidene)malononitrile (product from step A) in tetrahydrofuran was initially charged for the reaction.

The reaction was effected at 75° C. with 50 bar of hydrogen for 5 h.

The entire product solution was discharged from the reactor.

The composition of the product solution was determined by gas chromatography.

Step B2, 2nd Hydrogenation Stage): Full Hydrogenation of Product Solution from Step B1

150 ml of activated Raney cobalt alloy pellets were installed as a fixed bed in a 2 L pressure autoclave fitted with a catalyst cage. This catalyst had the following composition in weight percent (wt %), the proportions summing to 100 wt % based on the metals present:
cobalt: 75.9 wt %
aluminium: 20.0 wt %
chromium: 1.5 wt %
nickel: 2.6 wt %

A sieve fraction of the catalyst having a statistical distribution between 2.0 and 5.0 millimeters (mm) was employed, wherein up to 10% of the particles may be above the stated upper limit and up to 10% of the particles may be below the stated lower limit.

1 L of reaction solution (partially hydrogenated product from step B1 in THF) was initially charged for the reaction.

The reaction was effected at 100° C. with 100 bar of hydrogen for 5 h.

The composition of the product solution was determined by gas chromatography.

For use of TMP-PDA as a hardener in epoxy resin systems the product obtained was purified by distillation.

The yield of the two-stage hydrogenation was 85 wt % of TMP-PDA based on the employed substance 2-(2,2,6,6-tetramethylpiperidin-4-ylidene)malononitrile from step A.

Example 2: TMP-PDA as a Hardener in Epoxy Resin Systems

The epoxy resin employed was the standard resin Epikote 828 from Hexion having an epoxy equivalent weight of 188 g/eq. Said resin was blended in stoichiometric equality of the H equivalents with the hardener component TMP-PDA (cf. Table 1) and the glass transition temperature (Tg) was determined after a dwell time of one hour at a defined curing temperature (Table 2). The respective reaction conversions were determined via the recorded evolution of heat from the curing reaction in relation to the maximum evolution of heat (Table 3).

TABLE 1

| Ratio of resin to hardener | |
|---|---|
| Hardener component TMP-PDA (g) | 100 |
| Amount of epoxy resin (g) per 100 g of hardener | 441 |

TABLE 2

| Glass transition temperatures (Tg) after one hour of curing at various temperatures | |
|---|---|
| Tgmax (DSC) | 175° C. |
| Tg after 1 h 50° C. | 37° C. |
| Tg after 1 h 70° C. | 76° C. |
| Tg after 1 h 90° C. | 102° C. |
| Tg after 1 h 110° C. | 128° C. |
| Tg after 1 h 130° C. | 150° C. |
| Tg after 1 h 150° C. | 162° C. |

TABLE 3

| Conversions | |
|---|---|
| Conversion after 1 h 50° C. | 62% |
| Conversion after 1 h 70° C. | 80% |
| Conversion after 1 h 90° C. | 90% |
| Conversion after 1 h 110° C. | 95% |
| Conversion after 1 h 130° C. | 97% |
| Conversion after 1 h 150° C. | 100% |

As is readily apparent to a person skilled in the art from Table 1, Table 2 and Table 3, TMP-PDA is a suitable hardener component in epoxy resin systems.

The invention claimed is:

1. A process for producing 2-(2,2,6,6-tetramethylpiperidin-4-yl)propane-1,3-diamine, the process comprising the steps of
   A) reacting triacetonamine (TAA) and malononitrile to afford the intermediate 2-(2,2,6,6-tetramethylpiperidin-4-ylidene)malononitrile, and
   B) hydrogenating 2-(2,2,6,6-tetramethylpiperidin-4-ylidene)malononitrile in the presence of at least one catalyst.

2. The process according to claim 1, wherein the hydrogenation in step B) is performed at from 20-120° C. and at from 20-300 bar.

3. The process according to claim 2, wherein the hydrogenation in step B) is performed in two stages at from at 40-100° C. and at from 25-150 bar.

4. The process according to claim 3, wherein the hydrogenation in step B) is performed in two stages at from 20-120° C. and at from 20-300 bar.

5. The process according to claim 3, wherein the hydrogenation is performed at from 40-100° C. and from 25-150 bar in the first stage and at from 50-115° C. and from 50-200 bar in the second stage.

6. The process according to claim 3, wherein the hydrogenation is performed at from 60-90° C. and from 40-80 bar in the first stage and at from 80-110° C. and from 80-140 bar in the second stage.

7. The process according to claim 1, wherein the at least one catalyst is selected from nickel, copper, iron, palladium, rhodium, ruthenium or cobalt catalysts.

8. The process according to claim 1, wherein the at least one catalyst are palladium and/or cobalt catalysts.

9. The process according to claim 1, wherein the at least one catalyst are Raney-type catalysts or supported catalysts.

10. The process according to claim 1 wherein the at least one catalyst is a catalyst composed of activated Raney cobalt alloy pellets, wherein after activation the catalyst in its entirety has the following composition in weight percent (wt %), the proportions summing to 100 wt % based on the metals present:
    cobalt: 57 to 84 wt %
    aluminium: 10 to 40 wt %
    chromium: 1 to 2 wt %
    nickel: 2 to 4 wt %
    and
    with particle sizes of the catalyst, or the pellet particles, having a statistical distribution between 3 to 7 millimeters (mm), wherein up to 10 percent of the particles may also be outside the stated range of the stated lower limit or upper limit but also in each case up to 10 percent may be outside the stated range of the stated lower limit and upper limit.

11. The process according to claim 1, wherein the hydrogenation is performed in fixed-bed reactors.

12. The process according to claim 2, wherein the at least one catalyst is selected from the group consisting of nickel, copper, iron, palladium, rhodium, ruthenium or cobalt catalysts.

13. The process according to claim 3, wherein the at least one catalyst is selected from the group consisting of nickel, copper, iron, palladium, rhodium, ruthenium or cobalt catalysts.

14. The process according to claim 2, wherein the at least one catalyst is palladium and/or cobalt catalysts.

15. The process according to claim 2, wherein the at least one catalyst are Raney-type catalysts or supported catalysts.

16. The process according to claim 2, wherein the at least one catalyst is a catalyst composed of activated Raney cobalt alloy pellets, wherein after activation the catalyst in its entirety has the following composition in weight percent (wt %), the proportions summing to 100 wt % based on the metals present:
    cobalt: 57 to 84 wt %
    aluminium: 10 to 40 wt % chromium: 1 to 2 wt %
nickel: 2 to 4 wt %
and
with particle sizes of the catalyst, or the pellet particles, having a statistical distribution between 3 to 7 millimeters (mm), wherein up to 10 percent of the particles may also be outside the stated range of the stated lower limit or upper limit but also in each case up to 10 percent may be outside the stated range of the stated lower limit and upper limit.

17. The process according to claim 2, wherein the hydrogenation in step B) is performed in fixed-bed reactors selected from the group consisting of shaft furnaces, tray reactors or shell and tube reactors.

18. The process according to claim 4, wherein at least one catalyst selected from the group consisting of nickel, copper, iron, palladium, rhodium, ruthenium or cobalt catalysts.

19. The process according to claim 4, wherein the at least one catalyst is palladium and/or cobalt catalysts.

* * * * *